(12) United States Patent
Matsumoto et al.

(10) Patent No.: US 6,437,135 B1
(45) Date of Patent: Aug. 20, 2002

(54) PROCESS FOR PRODUCING QUINOLINECARBALDEHYDE

(75) Inventors: Hiroo Matsumoto; Takanori Shimizu; Yasutaka Takada, all of Chiba (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/868,904

(22) PCT Filed: Nov. 29, 1999

(86) PCT No.: PCT/JP99/06655

§ 371 (c)(1),
(2), (4) Date: Jul. 9, 2001

(87) PCT Pub. No.: WO00/42016

PCT Pub. Date: Jul. 20, 2000

(30) Foreign Application Priority Data

Jan. 14, 1999 (JP) .......................................... 11-007564

(51) Int. Cl.$^7$ .............................................. C07D 215/14
(52) U.S. Cl. ...................................................... 546/168
(58) Field of Search ......................................... 546/168

(56) References Cited

FOREIGN PATENT DOCUMENTS

| EP | 0 304 063 | 2/1989 |
| EP | 0 535 548 | 4/1993 |
| JP | 8-27114 | 1/1996 |

*Primary Examiner*—Zinna Northington Davis
(74) *Attorney, Agent, or Firm*—Oblon, Spivak, McClelland, Maier & Neustadt, P.C.

(57) ABSTRACT

A process for producing 2-cyclopropyl-4-(4-fluorophenyl)-quinoline-3-carbaldehyde, which entails oxidizing 2-cyclopropyl-4-(4-fluorophenyl)-3-hydroxymethylquinoline with a salt of a hypohalogenous acid in the presence of a quaternary ammonium salt.

14 Claims, No Drawings

PROCESS FOR PRODUCING QUINOLINECARBALDEHYDE

This application is a 371 application of PCT/JP 99/06655 filed Nov. 29, 1999.

BACKGROUND OF THE INVENTION

1. Technical Field

The present invention relates to a process for producing a quinolinecarbaldehyde. More particularly, it relates to a process for easily and efficiently producing 2-cyclopropyl-4-(4-fluorophenyl)-quinoline-3-carbaldehyde which is useful as an intermediate for the synthesis of a HMG-CoA reductase inhibitor as a cholesterol-lowering drug.

2. Background Art 2-cyclopropyl-4-(4-fluorophenyl)-quinoline-3-carbaldehyde is an intermediate useful as an intermediate for the synthesis of a HMG-CoA reductase inhibitor. Heretofore, as a method of oxidizing 2-cyclopropyl-4-(4-fluorophenyl)-3-hydroxymethylquinoline to 2-cyclopropyl-4-(4-fluorophenyl)-quinoline-3-carbaldehyde, an oxidation method employing chromic acid or a method of employing a dimethyl sulfoxide-dehydration agent (such as a Swern oxidation method), or a method of employing a nitroxyl radical-hypochlorite represented by TEMPO (2,2,6,6-tetramethyl-1-piperidinyloxy free radicals), has been used.

However, the above methods have a problem of waste liquid treatment due to formation of environmentally hazardous chromium ions or a problem of e.g. formation of badly smelling dimethyl sulfide, and in the case of nitroxyl radicals, the reagent is expensive and has a difficulty also in the chemical stability, and such can not be regarded as an industrially advantageous reaction.

SUMMARY OF THE INVENTION

Accordingly, the object of the present invention is to provide a process for simply and industrially advantageously producing 2-cyclopropyl-4-(4-fluorophenyl)-quinoline-3-carbaldehyde by oxidizing 2-cyclopropyl-4-(4-fluorophenyl)-3-hydroxymethylquinoline.

DETAILED DESCRIPTION OF THE PREFERRED EMBODIMENTS

The present inventors have studied various oxidation methods to solve such problems, and as a result, have found a production process which is free from the above-mentioned problem of waste liquid treatment or bad odor and which provides a good yield and is industrially advantageous, and they have arrived at the present invention.

Namely, the present invention provides a process for producing 2-cyclopropyl-4-(4-fluorophenyl)-quinoline-3-carbaldehyde of the formula (III):

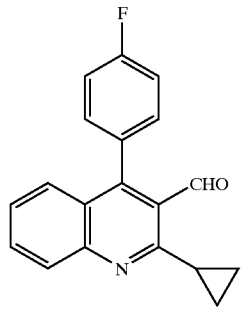

characterized by oxidizing 2-cyclopropyl-4-(4-fluorophenyl)-3-hydroxymethylquinoline of the formula

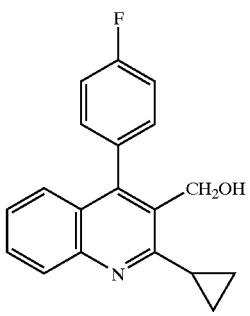

with a salt of a hypohalogenous acid in the presence of a quaternary ammonium salt of the formula (II):

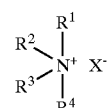

wherein each of $R^1$, $R^2$, $R^3$ and $R^4$ which are the same or different from one another, is a $C_{1-16}$ alkyl group or a benzyl group (the benzyl group may be substituted by a $C_{1-4}$ alkyl group, a $C_{1-4}$ alkoxy group or a halogen atom), and $X^-$ is a halogen ion, a sulfate ion or a methanesufonate ion.

According to the present invention, 2-cyclopropyl-4-(4-fluorophenyl)-quinoline-3-carbaldehyde which is a useful intermediate for the synthesis of a HMG-CoA reductase inhibitor, can be produced in good yield and industrially advantageously.

BEST MODE FOR CARRYING OUT THE INVENTION

Now, the present invention will be described in further detail.

Firstly, the terms for the respective substituents of $R^1$ $R^2$, $R^3$, $R^4$ and $X^-$ will be explained.

In this specification, "n" means normal, "i" iso, "s" secondary, "t" tertiary, "c" cyclo, and "o" ortho.

The $C_{1-4}$ alkyl group includes linear, branched and cyclic alkyl groups and may, for example, be methyl, ethyl, n-propyl, i-propyl, c-propyl, n-butyl, i-butyl, s-butyl, t-butyl, c-butyl, 1-methyl-c-propyl and 2-methyl-c-propyl, preferably methyl and ethyl.

The $C_{1-16}$ alkyl group includes linear, branched and cyclic alkyl groups and may, for example, be methyl, ethyl, n-propyl, i-propyl, c-propyl, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, 2-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl, n-heptyl, n-octyl, n-nonyl, n-decyl, n-undecyl, n-dodecyl, n-tridecyl, n-tetradecyl, n-pentadecyl and n-hexadecyl.

The $C_{1-4}$ alkoxy group includes linear, branched and cyclic alkoxy groups and may, for example, be methoxy, ethoxy, n-propoxy, i-propoxy, c-propoxy, n-butoxy, i-butoxy, s-butoxy, t-butoxy, c-butoxy, 1-methyl-c-propoxy and 2-methyl-c-propoxy, preferably methoxy and ethoxy.

The halogen atom may, for example, be a fluorine atom, a chlorine atom, a bromine atom and an iodine atom, preferably a chlorine atom and a bromine atom.

The halogen ion may, for example, be a fluorine ion, a chlorine ion, a bromine ion and an iodine ion, preferably a chlorine ion and a bromine ion.

The salt of a hypohalogenous acid may specifically be sodium hypochlorite, calcium hypochlorite, potassium hypochlorite and sodium hypobromite, preferably sodium hypochlorite, calcium hypochlorite and potassium hypochlorite.

Preferred $R_1$, $R_2$, $R_3$ and $R_4$ may be methyl, ethyl, n-propyl, i-propyl, n-butyl, n-octyl, n-dodecyl and benzyl.

Preferred $X^-$ may be a chlorine ion and a bromine ion.

The following process may be mentioned as a preferred process in the present invention.

(1) A process for producing 2-cyclopropyl-4-(4-fluorophenyl)-quinoline-3-carbaldehyde of the formula [III] characterized by oxidizing 2-cyclopropyl-4-(4-fluorophenyl)-3-hydroxymethylquinoline of the formula [I] with sodium hypochlorite, calcium hypochlorite or potassium hypochlorite in the presence of a quaternary ammonium salt of the formula [II].

Now, a specific process for producing 2-cyclopropyl-4-(4-fluorophenyl)-quinoline-3-carbaldehyde will be explained.

The quaternary ammonium salt is added to a solution comprising 2-cyclopropyl-4-(4-fluorophenyl)-3-hydroxymethylquinoline and a solvent for the reaction, followed by stirring, and the salt of a hypohalogenous acid is added thereto, followed by stirring, whereby the desired 2-cyclopropyl-4-(4-fluorophenyl)-quinoline-3-carbaldehyde can be produced.

The solvent for the reaction is not particularly limited so long as it does not affect the reaction. For example, nitriles such as acetonitrile, propionitrile and butylonitrile, ketones such as acetone, methyl ethyl ketone and methyl isobutyl ketone, aromatic hydrocarbons such as benzene, toluene, xylene, mesitylene, chlorobenzene and o-dichlorobenzene, aliphatic hydrocarbons such as n-hexane, cyclohexane, n-octane and n-decane, esters such as methyl acetate, ethyl acetate and propyl acetate, halogenated hydrocarbons such as dichloromethane, dichloroethane and chloroform, ethers such as tetrahydrofuran, diethyl ether, t-butyl methyl ether and dimethoxy ethane, an amide such as N,N-dimethylformamide, N,N-dimethylacetoamide and N-methyl pyrrolidone, ureas such as 1,3-dimethylimidazolidinone and tetramethyl urea, preferably esters such as methyl acetate, ethyl acetate and propyl acetate, halogenated hydrocarbons such as dichloromethane, dichloroethane and chloroform, aromatic hydrocarbons such as toluene and xylene, and ketones such as acetone, methyl ethyl ketone and methyl isobutyl ketone, may, be mentioned.

Further, these solvents for the reaction may be used alone or in combination.

The amount of the solvent for the reaction to be used is within a range of from 1 to 200 times (w/w), preferably within a range of from 2 to 50 times (w/w), of the substrate (2-cyclopropyl-4-(4-fluorophenyl)-3-hydroxymethylquinoline).

The quaternary ammonium salts may not necessarily be used alone, and two or more of them may be used in combination. The amount of the quaternary ammonium salt is from 0.005 to 5 equivalents, preferably from 0.05 equivalent to 0.5 equivalent, based on the substrate.

The amount of the salt of a hypohalogenous acid is from 1.05 to 5 equivalents, preferably from 1.1 to 2 equivalents, based on the substrate.

The reaction temperature is within a range of from −20° C. to 100° C., preferably from 10° C. to 70° C.

The reaction time varies depending upon the solvent to be used, the type and amount of the quaternary ammonium salt, the reaction temperature, etc. from the viewpoint of an industrial process, it is preferably within 8 hours.

After completion of the reaction, water is added, followed by extraction with a solvent for extraction, such as ethyl acetate, dichloromethane or toluene, drying and concentration under reduced pressure to obtain the desired 2-cyclopropyl-4-(4-fluorophenyl)-quinoline-3-carbaldehyde.

If necessary, recrystallization is carried out from a solvent for recrystallization, such as a methanol/water mixed solvent or a toluene/n-hexane mixed solvent, or crystals obtained by distilling off the solvent for extraction are washed with e.g. i-propyl ether or c-hexane, whereby 2-cyclopropyl-4-(4-fluorophenyl)-quinoline-3-carbaldehyde of high purity can be isolated.

Now, the present invention will be described in detail with reference to Examples, but the present invention is by no means restricted to such specific Examples.

The HPLC analysis of 2-cyclopropyl-4-(4-fluorophenyl)-quinoline-3-carbaldehyde, was carried out under the following conditions.

Column: Nucleosil 100 5C–18
Eluent: Acetonitrile/water (3:2, v/v)
Temperature: 40° C.
Flow rate: 1 ml/min
Retention time: 30.4 min

EXAMPLE 1

Oxidation of an Alcohol to an Aldehyde by Sodium Hypochlorite in the Presence of Tetra N-butyl Ammonium Bromide 0.15 g (0.47 mmol) of tetra n-butyl ammonium bromide was added to a mixed solution of 0.8 g (2.73 mmol) of 2-cyclopropyl-4-(4-fluorophenyl)-3-hydroxymethylquinoline in ethyl acetate (7.5 ml) and water (3.5 ml), followed by stirring at 15° C.

Then, 4.2 g (5.41 mmol) of sodium hypochlorite (9.6%) was added thereto, followed by stirring for one hour, and then 20 ml of water was added, followed by extraction with 20 ml of ethyl acetate.

The aqueous layer was extracted again with 20 ml of ethyl acetate.

The organic layers were put together and washed with 20 ml of water, and then dried over magnesium sulfate, and the solvent was distilled off under reduced pressure.

The residue was dissolved in 32 ml of methanol, and 10 ml of water was dropwise added thereto, followed by cooling to 0° C.

The obtained crystals were collected by filtration to obtain 0.62 g (yield: 78%) of 2-cyclopropyl-4-(4-fluorophenyl)-quinoline-3-carbaldehyde as slightly yellow crystals.

(HPLC purity: 99.6%) (Melting point: 152° C.)

EXAMPLE 2

0.15 g (0.47 mmol) of tetra n-butyl ammonium bromide was added to a mixed solution of 2.4 g (8.19 mmol) of 2-cyclopropyl-4-(4-fluorophenyl)-3-hydroxymethylquinoline in ethyl acetate (22.5 ml) and water (10.5 ml), followed by stirring at 15° C.

Then, 12.6 g (16.23 mmol) of sodium hypochlorite (9.6%) was added thereto, followed by stirring for 3 hours, and then 60 ml of water was added, followed by extraction with 60 ml of ethyl acetate.

The aqueous layer was extracted again with 60 ml of ethyl acetate.

The organic layers were put together, washed with 60 ml of water, and then dried over anhydrous magnesium sulfate, and the solvent was distilled off under reduced pressure.

The residue was dissolved in 110 ml of methanol, and 35 ml of water was dropwise added thereto, followed by cooling to 0° C.

The obtained crystals were collected by filtration to obtain 2.03 g (yield: 85%) of 2-cyclopropyl-4-(4-fluorophenyl)-quinoline-3-carbaldehyde as slightly yellow crystals.

(HPLC purity: 99.8%) (Melting point: 152° C.)

What is claimed is:

1. A process for producing 2-cyclopropyl-4-(4-fluorophenyl)-quinoline-3-carbaldehyde of the formula (III):

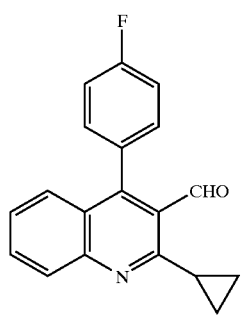

(III)

which comprises oxidizing 2-cyclopropyl-4-(4-fluorophenyl)-3-hydroxymethylquinoline of the formula (I):

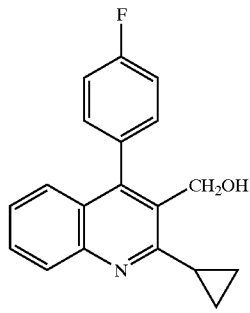

(I)

with a salt of a hypohalogenous acid in the presence of a quaternary ammonium salt of the formula (II):

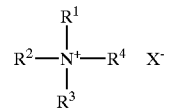

(II)

wherein each of $R^1$, $R^2$, $R^3$ and $R^4$, which are each the same or different from each other, is a $C_1$–$C_{16}$ alkyl or benzyl, which benzyl is optionally substituted by $C_1$–$C_4$ alkyl $C_1$–$C_4$ alkoxy or halogen; and $X^-$ is halogen, sulfate or methanesulfonate ion.

2. The process of claim 1, wherein the salt of a hypohalogenous acid is sodium hypochlorite, calcium hypochlorite or potassium hypochlorite.

3. The process of claim 1, wherein $R^1$, $R^2$, $R^3$ and $R^4$ are each selected from the group consisting of methyl, ethyl, n-propyl, isopropyl, n-butyl, n-octyl, n-dodecyl and benzyl.

4. The process of claim 1, wherein $X^-$ is chloride or bromide ion.

5. The process of claim 1, which is conducted in a solvent comprising nitriles, ketones, aromatic hydrocarbons, aliphatic hydrocarbons, esters, ethers, amides, ureas or halogenated hydrocarbons.

6. The process of claim 1, which is conducted at from −20° C. to 100° C.

7. The process of claim 1, which is conducted at from 10° C. to 70° C.

8. The process of claim 1, which further comprises after completion of reaction, adding water, extracting with organic solvent, drying and concentrating under reduced pressure to obtain said 2-cyclopropyl-4-(4-fluorophenyl)-quinoline-3-carbaldehyde.

9. The process of claim 8, which further comprises recrystallizing said 2-cyclopropyl-4-(4-fluorophenyl)-quinoline-3-carbaldehyde.

10. The process of claim 1, having a yield of 78 to 85% of 2-cyclopropyl-4-(4-fluorophenyl)-quinoline-3-carbaldehyde.

11. A reaction mixture, comprising:

a) 2-cyclopropyl-4-(4-fluorophenyl)-3-hydroxymethylquinoline, b) a salt of a hypohalogenous acid, and c) a quaternary ammonium salt having the formula (II)

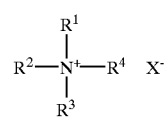
(II)

wherein each of $R^1$, $R^2$, $R^3$ and $R^4$, which are each the same or different from each other, is a $C_1$–$C_{16}$ alkyl or benzyl, which benzyl is optionally substituted by $C_1$–$C_4$ alkyl, $C_1$–$C_4$ alkoxy or halogen; and X is halogen, sulfate or methanesulfonate ion.

12. The reaction mixture of claim 11, wherein the salt (b) is sodium hypochlorite, calcium hypochlorite or potassium hypochlorite.

13. The reaction mixture of claim 11, wherein for quaternary ammonium salt (c), $X^-$ is chloride or bromide ion.

14. The reaction mixture of claim 11, which further comprises a solvent comprising nitrites, ketones, aromatic hydrocarbons, aliphatic hydrocarbons, halogenated hydrocarbons, esters, ethers, amides or ureas.

* * * * *